(12) United States Patent
El-Siblani

(10) Patent No.: US 8,110,135 B2
(45) Date of Patent: Feb. 7, 2012

(54) PROCESS AND FREEFORM FABRICATION SYSTEM FOR PRODUCING A THREE-DIMENSIONAL OBJECT

(75) Inventor: Ali El-Siblani, Dearborn Heights, MI (US)

(73) Assignee: Envisiontec GmbH, Gladbeck (DE)

( * ) Notice: Subject to any disclaimer, the term of this patent is extended or adjusted under 35 U.S.C. 154(b) by 74 days.

(21) Appl. No.: 12/290,003

(22) Filed: Oct. 24, 2008

(65) Prior Publication Data

US 2009/0130449 A1 May 21, 2009

Related U.S. Application Data

(60) Provisional application No. 61/000,603, filed on Oct. 26, 2007.

(51) Int. Cl.
*B29C 35/08* (2006.01)
(52) U.S. Cl. ............... 264/401; 264/480; 425/135
(58) Field of Classification Search ............ 264/401, 264/460; 425/135
See application file for complete search history.

(56) References Cited

U.S. PATENT DOCUMENTS

| | | | |
|---|---|---|---|
| 4,837,379 A | 6/1989 | Weinberg |
| 4,929,402 A | 5/1990 | Hull |
| 4,999,143 A | 3/1991 | Hull et al. |
| 5,093,130 A | 3/1992 | Fujii et al. |
| 5,137,662 A | 8/1992 | Hull et al. |
| 5,139,338 A | 8/1992 | Pomerantz et al. |
| 5,143,663 A | 9/1992 | Leyden et al. |
| 5,157,423 A | 10/1992 | Zur |
| 5,171,490 A | 12/1992 | Fudim |
| 5,173,266 A | 12/1992 | Kenney |
| 5,174,931 A | 12/1992 | Almquist et al. |
| 5,236,637 A | 8/1993 | Hull |
| 5,247,180 A | 9/1993 | Mitcham et al. |
| 5,248,456 A | 9/1993 | Evans, Jr. et al. |
| 5,263,130 A | 11/1993 | Pomerantz et al. |
| 5,268,994 A | 12/1993 | Keskes |

(Continued)

FOREIGN PATENT DOCUMENTS

DE 41 05 314 8/1991

(Continued)

OTHER PUBLICATIONS

International Preliminary Report on Patentability for PCT/EP2008/009041, dated Apr. 27, 2010.

(Continued)

*Primary Examiner* — Maria Veronica Ewald
*Assistant Examiner* — Robert J Grun
(74) *Attorney, Agent, or Firm* — Hansen IP Law PLLC

(57) ABSTRACT

The present invention describes a process for producing a three-dimensional object, comprising: providing a material to be solidified, the material comprising a filler and a binder; delivering electromagnetic radiation and/or synergistic stimulation in a pattern or an image to a building region for solidifying said material; wherein said delivering of electromagnetic radiation and/or synergistic stimulation is performed selectively to a defined area or volume of said material to be solidified; and wherein an energy density of electromagnetic radiation and/or synergistic stimulation is varied within said pattern or image and/or between patterns or images of different building regions of said material. The present invention may be directed also to a system where different first and second materials are to be solidified. The present invention further provides a freeform fabrication system, and a freeform three-dimensional object having unique properties as well as products derived therefrom, such as sintered products.

27 Claims, 4 Drawing Sheets

U.S. PATENT DOCUMENTS

| | | | |
|---|---|---|---|
| 5,289,214 A | 2/1994 | Zur | |
| 5,298,208 A | 3/1994 | Sibley et al. | |
| 5,306,446 A | 4/1994 | Howe | |
| 5,345,391 A | 9/1994 | Hull et al. | |
| 5,360,981 A | 11/1994 | Owen et al. | |
| 5,391,072 A | 2/1995 | Lawton et al. | |
| 5,447,822 A | 9/1995 | Hull et al. | |
| 5,510,077 A | 4/1996 | Dinh et al. | |
| 5,529,473 A | 6/1996 | Lawton et al. | |
| 5,545,367 A | 8/1996 | Bae et al. | |
| 5,569,431 A | 10/1996 | Hull | |
| 5,571,471 A | 11/1996 | Hull | |
| 5,630,981 A | 5/1997 | Hull | |
| 5,651,934 A | 7/1997 | Almquist et al. | |
| 5,653,925 A | 8/1997 | Batchelder | |
| 5,823,778 A | 10/1998 | Schmitt et al. | |
| 5,858,746 A | 1/1999 | Hubbell et al. | |
| 5,891,382 A | 4/1999 | Almquist et al. | |
| 5,894,036 A | 4/1999 | Tylko | |
| 5,902,537 A | 5/1999 | Almquist et al. | |
| 5,945,058 A | 8/1999 | Manners et al. | |
| 5,980,813 A | 11/1999 | Narang et al. | |
| 6,013,099 A | 1/2000 | Dinh et al. | |
| 6,027,324 A | 2/2000 | Hull | |
| 6,048,487 A | 4/2000 | Almquist et al. | |
| 6,051,179 A | 4/2000 | Hagenau | |
| 6,153,034 A | 11/2000 | Lipsker | |
| 6,158,946 A | 12/2000 | Miyashita | |
| 6,171,610 B1 | 1/2001 | Vacanti et al. | |
| 6,280,727 B1 | 8/2001 | Prior et al. | |
| 6,281,903 B1 | 8/2001 | Martin et al. | |
| 6,334,865 B1 | 1/2002 | Redmond et al. | |
| 6,352,710 B2 | 3/2002 | Sawhney et al. | |
| 6,391,245 B1 | 5/2002 | Smith | |
| 6,500,378 B1 | 12/2002 | Smith | |
| 6,547,552 B1 | 4/2003 | Fudim | |
| 6,630,009 B2 | 10/2003 | Moussa et al. | |
| 6,764,636 B1 | 7/2004 | Allanic et al. | |
| 6,833,231 B2 | 12/2004 | Moussa et al. | |
| 6,833,234 B1 | 12/2004 | Bloomstein et al. | |
| 6,942,830 B2 | 9/2005 | Mülhaupt et al. | |
| 6,974,656 B2 | 12/2005 | Hinczewski | |
| 6,989,225 B2 | 1/2006 | Steinmann | |
| 7,052,263 B2 | 5/2006 | John | |
| 7,073,883 B2 | 7/2006 | Billow | |
| 7,133,041 B2 | 11/2006 | Kaufman et al. | |
| 7,195,472 B2 | 3/2007 | John | |
| 7,215,430 B2 | 5/2007 | Kacyra et al. | |
| 7,261,542 B2 | 8/2007 | Hickerson et al. | |
| 7,467,939 B2* | 12/2008 | Sperry et al. | 425/375 |
| 2001/0028495 A1 | 10/2001 | Quate et al. | |
| 2001/0048183 A1 | 12/2001 | Fujita | |
| 2002/0028854 A1 | 3/2002 | Allanic et al. | |
| 2002/0155189 A1 | 10/2002 | John | |
| 2003/0067539 A1 | 4/2003 | Doerfel et al. | |
| 2003/0074096 A1 | 4/2003 | Das et al. | |
| 2003/0205849 A1 | 11/2003 | Farnworth | |
| 2004/0008309 A1 | 1/2004 | Yamahara et al. | |
| 2005/0023710 A1* | 2/2005 | Brodkin et al. | 264/16 |
| 2005/0208168 A1 | 9/2005 | Hickerson et al. | |
| 2005/0248061 A1 | 11/2005 | Shkolnik et al. | |
| 2005/0248062 A1 | 11/2005 | Shkolnik et al. | |
| 2005/0288813 A1 | 12/2005 | Yang et al. | |
| 2006/0078638 A1 | 4/2006 | Holmboe et al. | |
| 2006/0192312 A1 | 8/2006 | Wahlstrom et al. | |
| 2006/0239588 A1 | 10/2006 | Hull et al. | |
| 2006/0249884 A1 | 11/2006 | Partanen et al. | |
| 2007/0074659 A1 | 4/2007 | Wahlstrom | |
| 2007/0075458 A1 | 4/2007 | Wahlstrom et al. | |
| 2007/0075459 A1 | 4/2007 | Reynolds et al. | |
| 2007/0075460 A1 | 4/2007 | Wahlstrom et al. | |
| 2007/0075461 A1 | 4/2007 | Hunter et al. | |
| 2007/0077323 A1 | 4/2007 | Stonesmith et al. | |
| 2007/0120842 A1 | 5/2007 | Hess | |
| 2007/0257055 A1 | 11/2007 | Scott et al. | |
| 2007/0259066 A1 | 11/2007 | Sperry et al. | |
| 2008/0038396 A1 | 2/2008 | John et al. | |
| 2008/0054531 A1* | 3/2008 | Kerekes et al. | 264/401 |
| 2008/0169586 A1 | 7/2008 | Hull et al. | |
| 2008/0169589 A1 | 7/2008 | Sperry et al. | |
| 2008/0170112 A1 | 7/2008 | Hull et al. | |
| 2008/0179786 A1 | 7/2008 | Sperry et al. | |
| 2008/0179787 A1 | 7/2008 | Sperry et al. | |
| 2008/0181977 A1 | 7/2008 | Sperry et al. | |
| 2008/0206383 A1 | 8/2008 | Hull et al. | |
| 2008/0217818 A1 | 9/2008 | Holmboe et al. | |
| 2008/0226346 A1* | 9/2008 | Hull et al. | 399/177 |
| 2008/0231731 A1 | 9/2008 | Hull | |
| 2008/0309665 A1 | 12/2008 | Gregory, II | |

FOREIGN PATENT DOCUMENTS

| | | |
|---|---|---|
| DE | 41 02 257 | 7/1992 |
| DE | 41 25 534 A1 | 2/1993 |
| DE | 93 19 405 | 5/1994 |
| DE | G 93 19 405.6 | 5/1994 |
| DE | 43 40 108 | 8/1997 |
| DE | 197 27 554 | 1/1999 |
| DE | 299 11 122 U1 | 11/1999 |
| DE | 198 38 797 | 3/2000 |
| DE | 199 29 199 A1 | 1/2001 |
| DE | 100 03 374 | 8/2001 |
| DE | 100 18 987 | 10/2001 |
| DE | 201 06 887 | 10/2001 |
| DE | 699 09 136 T2 | 5/2004 |
| DE | 10 2004 022 961 A1 | 12/2005 |
| EP | 0 250 121 | 12/1987 |
| EP | 0 426 363 | 5/1991 |
| EP | 0 435 564 A2 | 7/1991 |
| EP | 0 466 422 A1 | 1/1992 |
| EP | 0 484 086 A1 | 5/1992 |
| EP | 1 250 995 | 10/2002 |
| EP | 1 250 997 A1 | 10/2002 |
| EP | 1 270 185 | 1/2003 |
| EP | 1 192 041 B1 | 3/2003 |
| EP | 1 156 922 B1 | 6/2003 |
| EP | 1 338 846 | 8/2003 |
| EP | 1674243 A2 | 6/2006 |
| EP | 1 849 587 | 10/2007 |
| EP | 1 880 830 | 1/2008 |
| EP | 1 894 704 | 3/2008 |
| EP | 1 950 032 | 7/2008 |
| EP | 2 011 631 | 1/2009 |
| FR | 2 254 194 | 7/1975 |
| FR | 2 583 334 | 12/1986 |
| FR | 2 634 686 | 2/1990 |
| FR | 2 692 053 | 12/1993 |
| JP | 04371829 | 12/1992 |
| JP | 08192469 | 7/1996 |
| WO | WO 95/11007 | 4/1995 |
| WO | WO-95/15841 | 6/1995 |
| WO | WO-96/00422 | 1/1996 |
| WO | WO-01/00390 A1 | 1/2001 |
| WO | WO-01/12679 | 2/2001 |
| WO | WO-01/72501 A1 | 10/2001 |
| WO | WO-03/059184 | 7/2003 |
| WO | WO-2005/110722 A1 | 11/2005 |
| WO | 2009053100 A1 | 4/2009 |

OTHER PUBLICATIONS

K. Takahashi, "A New Application of DMD to Photolithography and Rapid Prototyping System," Institute of Electronics, Information, and Communication Engineers.

Wohlers Report 2000, "Rapid Prototyping & Tooling State of the Industry Annual Worldwide Progress Report", T. Wohlers, Wohlers Association, Inc., Fort Collins, Colorado (2000).

Stark, G.B., et al., "Biological Matrices and Tissue Reconstruction", Springer Publications, Berlin (1998).

Sachs, E., et al., "Three Dimensional Printing: Rapid Tooling and Prototypes Directly from CAD Model", Journal of Engineering for Industry, 114:481-488 (1992).

Kuhtreiber, W., Ph.D., et al., "Cell Encapsulation Technology and Therapeutics", Birkhauser, Boston (1998).

Landers, R., and Mulhaupt, R., "Desktop Manufacturing of Complex Objects, Prototypes and Biomedical Scaffolds by Means of Computer-Assisted Design Combined with Computer-Guided 3D Plotting of Polymers and Reactive Oligomers," Macromolecular Materials and Engineering, 282:17-22 (2000).

Okada, T., and Ikada, Y., "Tissue Reactions to Subcutaneously Implanted, Surface-Modified Silicones", Journal of Biomedical Materials Research, 27:1509-1518 (1993).

Relou, I.A., et al., "Effect of Culture Conditions on Endothelial Cell Growth and Responsiveness", Tissue & Cell, 30(5):525-538 (1998).

Nikolaychik, V.V., et al., A New, Cryopreciptate Based Coating for Improved Endothelial Cell Attachment and Growth on Medical Grade Artificial Surfaces:, ASAIO Journal, 40:M846-M852 (1994).

Burns, "Automatic Fabrication Improving Productivity in Manufacturing", 1993 (ISBN 0-13-119462-3).

Opposition to EP 1,849,587, dated Apr. 8, 2010.

C. Sun, et al., "Projection Micro-Stereolithography Using Digital Micro-Mirror Dynamic mask," Sensors and Actuators A 121 (2005) 113-120.

S. Ventura, et al., "Freeform Fabrication of Functional Silicon Nitride Components by Direct Photoshaping," Mat. Res. Sol. Symp. Proc., vol. 625 (2000).

K. Takahashi, "A New Application of DMD to Photolithography and Rapid Prototyping System," Institute of Electronics, Information, and Communication Engineers, (2001).

* cited by examiner

US 8,110,135 B2

PROCESS AND FREEFORM FABRICATION SYSTEM FOR PRODUCING A THREE-DIMENSIONAL OBJECT

FIELD

The present invention relates to a process and a device for producing at least one three-dimensional object by solidifying a solidifiable material which comprises a filler and a binder. The process and the device are particularly suitable for medical applications, such as for producing implants, bone substitutes and in particular for producing dental products.

BACKGROUND ART

Known processes and devices for producing at least one three-dimensional object by solidifying a solidifiable material are sometimes referred to as rapid prototyping and manufacturing techniques, and sometimes they are more specifically referred to as stereolithography, laser sintering, fused deposition modelling, selective light modulation and the like, without being limited thereto. In the following, processes, devices and systems of this art are commonly referred to as "freeform fabrication".

Sometimes and especially in situations affording three-dimensional objects of higher strength formed by freeform fabrication, the material to be solidified comprises a filler and a binder, and the resulting composite product being solidified may be further treated or not.

For example, WO 03/059184A2 describes a production of dental restorations and other custom objects by freeform fabrication methods and systems, involving a required deposition of a layer comprising photocurable material and ceramic material and selectively exposing the layer to radiation in a desired pattern.

However, previous freeform fabrication systems described in WO 03/059184A2 and in other documents dealing with composite materials to be solidified have found to be unsatisfactory. In particular the presence of a particulate of fibrous filler in admixture with a binder in the material to be solidified has been identified by the present inventors to encounter difficulties, if three-dimensional objects produced by freeform fabrication techniques shall be produced with a desirable accuracy and mechanical strength in a reliable manner.

SUMMARY

The present invention addresses this demand, and an object lies with the provision of a process and a device for producing a three-dimensional object by solidifying a material comprising a filler and a binder, which process or device is improved in terms of reliability.

In accordance with an embodiment the present invention provides a process for producing a three-dimensional object, comprising: providing a material to be solidified, the material comprising a filler and a binder; delivering electromagnetic radiation and/or synergistic stimulation in a pattern or an image to a building region for solidifying said material; wherein said delivering of electromagnetic radiation and/or synergistic stimulations performed selectively to a defined area or volume of said material to be solidified; and wherein an energy density of electromagnetic radiation and/or synergistic stimulation is varied within said pattern or image and/or between patterns or images of different building regions of said material.

In an alternative embodiment directed to a system where different first and second materials are to be solidified, there is provided a process for producing a three-dimensional object, comprising: providing a first material to be solidified for generating at least a part of a desired three-dimensional object structure, the material comprising a filler and a binder; providing a second material, different from said first material, to be solidified as another part of the desired three-dimensional object structure or as an auxiliary support structure; solidifying said first and second materials by means of electromagnetic radiation and/or synergistic stimulation delivered selectively to respectively defined areas or volumes of said first and second materials; wherein energy densities of electromagnetic radiation and/or synergistic stimulation are varied between said respectively defined areas or volumes of said first and second materials for solidification.

The present invention further provides a freeform fabrication system, comprising: a material to be solidified, the material comprising a filler and a binder; a electromagnetic radiation and/or synergistic stimulation delivery device capable of delivering electromagnetic radiation and/or synergistic stimulation in a pattern or an image to a building region for solidifying said material; wherein said electromagnetic radiation and/or synergistic stimulation delivery device is designed to selectively deliver electromagnetic radiation and/or synergistic stimulation to a defined area or volume of said material to be solidified; wherein an energy density of electromagnetic radiation and/or synergistic stimulation is varied within said pattern or image, and/or between patterns or images of different building regions of said material.

Likewise, in the alternative embodiment directed to different first and second materials to be solidified, there is provided a freeform fabrication system, comprising: a first material to be solidified for generating at least a part of a desired three-dimensional object structure, the material comprising a filler and a binder; a second material, different from said first material, to be solidified as another part of the desired three-dimensional object structure or as an auxiliary support structure; and a electromagnetic radiation and/or synergistic stimulation delivery device capable of delivering electromagnetic radiation and/or synergistic stimulation selectively to defined areas or volumes of said first and second materials, respectively;

wherein energy densities of electromagnetic radiation and/or synergistic stimulation is varied between said respectively defined areas or volumes of said first and second materials for solidification.

According to a further embodiment the present invention provides a freeform fabrication system, comprising: a material to be solidified, the material comprising a filler and a binder; an electromagnetic radiation and/or synergistic stimulation delivery device capable of delivering electromagnetic radiation and/or synergistic stimulation which allows an additive generation of a three-dimensional object by successive solidification of said material; wherein said electromagnetic radiation and/or synergistic stimulation delivery device is based on a mask exposure system or a projection system.

The present invention further provides a freeform three-dimensional object formed from a solidifiable material comprising a filler and a binder by electromagnetic radiation and/or synergistic stimulation according to any one of the above mentioned embodiments. By the processes and fabrication systems according to the present invention, a three-dimensional object having an improved combination of product characteristics is obtained, in particular a homogenous mechanical strength throughout the object (albeit being formed by an additive generative process) combined with a high dimensional accuracy both before and after post-treatment, in particular if the post-treatment is sintering.

Principles, advantages and preferred embodiments will be described in further detail below.

In accordance with the present invention, it has been found that solidification behaviour in parts of areas or volumes defining a building region is critically affected by a presence (and possibly a type) or absence of a particulate or fibrous filler substance depending on conditions of electromagnetic radiation and/or synergistic stimulation in certain areas or volumes being particularly relevant for a accurate solidification or differentiated solidification. Mechanisms affecting relevant process and product characteristics can be well adjusted according to the present invention by actively and selectively controlling energy density delivered by the electromagnetic radiation and/or synergistic stimulation (also known as "exposure energy density", measured in a unit of $J/m^2$ or $mJ/cm^2$ or $mW/dm^2$, in the following briefly denoted "energy density"). With the energy density being at least partially varied, it is possible to produce three-dimensional objects having well-balanced counter-acting properties such as homogeneous mechanical strength and high dimensional accuracy, i.e. avoiding local distortions that may be caused by a differential influence of particulate or fibrous filler on electromagnetic radiation and/or synergistic stimulation activity. In accordance with the present invention, variation of energy density means that at least in part(s) of an exposed pattern or image or at least in part(s) of different building regions, there is an active spatial modification of an energy density relative to an unmodified/unvaried exposure. This variation in turn means that within the totality of a building region or of different building regions of a three-dimensional object, there are parts having received less energy density for primary solidification than other parts. A variation of energy density can be imposed gradually, step-wise, selectively in a part of a defined pattern or image while the remaining part is kept unmodified/unvaried, or selectively in one or more building regions relative to other building region(s), or any combination thereof. Assuming a building region being defined by a selectively exposed area or volume with dimensions of X, Y and Z relative to the whole built volume of a three-dimensional object to be formed, variation of energy density may be imposed in the projected pattern or image in XY plane, in XZ plane, in YZ plane or otherwise structured plane or curved surface. Alternatively or in addition to this variation within a building region, variation between patterns or images of different building regions of the material to be solidified may be imposed. As noted, the active variation of energy density according to the present invention becomes particularly relevant owing to the presence and/or the spatial location and/or nature of the filler substance contained in the composite material together with the binder, under the action of electromagnetic and/or synergistic radiation. It is possible, according to the present invention, to counter-balance and to control critical phenomena of a particulate or fibrous filler provoked by electromagnetic radiation and/or synergistic stimulation at certain locations, including, but not limited to absorbance, reflection and/or scattering phenomena.

Owing to the above mentioned special circumstances based on the use of a composite material containing a particulate or fibrous filler in admixture with a binder to be solidified, variation of energy density of the electromagnetic radiation and/or synergistic stimulation may be controlled, for example by an appropriate control unit or by manual operation, depending on at least one of the following criteria, alone or in combination:

(i) Type and/or amount of filler contained in a material to be solidified:

For example, depending on whether or to which extent the filler absorbs, reflects, or scatters electromagnetic and/or synergistic radiation, energy density may be varied depending on the spatial location of the building region where solidification shall take place. For example, energy density may be increased at locations within a building region where absorption phenomena prevail over reflection or scattering phenomena. Conversely, energy density may be decreased at locations within the building region where reflection and/or scattering phenomena prevail over absorption phenomena. Whether absorption or reflection/scattering phenomena prevail may, inter alia, depend on the type of filler. Therefore, the active variation of energy density according to the present invention enables an adaptation to the use of a wide variety of different filler substances, including but not limited to ceramics, glass, solid polymer particles, metals, metal alloys as described in further detail below, and including modified forms such as making absorptive metal particles reflective by means of suitable coatings, e.g. by waxes, coupling agents, polymers and the like. The present invention also allows to take account of the size and/or the amount of a filler substance being present in a particulate (or powder) or fibrous form, as well as to respond to situations such as filler sedimentation during the fabrication process. Moreover, the present invention provides an advantage that a three-dimensional object can be more reliably produced by using two or more different materials to be solidified, among which at least one comprises a filler, yet with one fabrication system while making use of adapted varied energy density.

(ii) Type and/or amount of binder:

Likewise, in combination with the specific type and/or amount of filler substance, critical solidification criteria including absorption, reflection and/or scattering phenomena can be actively influenced depending on the type and/or amount of binder with respect to a certain location within a building region.

(iii) Hardening depth:

It has been found that owing to the presence of filler substance, and in particular with an increasing amount thereof, penetration depth ($D_p$) and minimum exposure dose required to cause gelation ($E_c$) may be substantially reduced in a given hardening depth direction, unless an active variation of energy density according to the present invention is performed. In a particular embodiment, energy density variation may be performed by, firstly, actively withdrawing energy density, e.g. by cooling or by interfering radiation, selectively at the surface where the electromagnetic radiation and/or synergistic stimulation impinges on the building region (for example a surface of a photopolymerizable or photocurable resin containing the filler substance) to thereby relatively enhance energy density towards the depth direction, secondly by shifting the focal plane of the exposure system to an area or plane away from the afore-mentioned surface, thirdly by appropriately superimposing electromagnetic radiation and/or synergistic stimulation fields to be concentrated at a certain desired hardening depth, and/or fourthly by applying an additional infrared electromagnetic radiation (i.e. heat) from the side opposite to the exposure direction of the electromagnetic radiation and/or synergistic stimulation intended for material solidification, in order to superimpose a temperature gradient with a higher temperature at increased hardening depths. By one or more of these or equivalent means, it is possible to counteract predominant hardening at the exposed surface region, and to more homogenize energy density in a desired hardening depth direction.

(iv) Presence or absence of underlying or overlying solidified and filler-containing material:

Depending on whether previously solidified filler-containing material has absorptive, or reflective and scattering characteristics, the local-specific presence or absence of such underlying/overlying filler-containing material can be taken into account by an appropriate variation. When absorptive, underlying/overlying portions may be rather overexposed by a relatively higher energy density, whereas when reflective and scattering, they may be rather underexposed by relatively lower energy density, respectively compared to other portions within the pattern or image or compared to other building regions where such underlying/overlying solidified filler-containing material is not present (e.g. at overhang portions or cavity portions of the object structure to be formed).

(v) Size of the defined area or volume of the material to be solidified in the building region:

In a given unmodified fabrication system, larger exposure areas or volumes tend to receive a larger amount of energy per unit area, relative to smaller or more delicate exposure areas or volumes. This tendency may be affected by the presence of filler in the exposed areas or volumes. Therefore, at least a partial area or volume of a building region having a larger size can be underexposed in terms of energy density relative to co-exposed smaller building regions.

(vi) Delivery of electromagnetic radiation and/or synergistic stimulation to area or volume regions as opposed to boundary regions of the three-dimensional object to be formed:

These distinct regions exhibit significantly different characteristics in terms of absorption, reflection and/or scattering performances, as well as in terms of shrinkage performances. Roughly, these characteristics are affected relatively isotropically within area or volume regions, but relatively anisotropically at boundary regions caused by the then present edges.

An example may be explained in case of using a ceramic filler material having reflective and scattering characteristics: Given a certain amount of energy or energy density necessary to solidify the binder of the material in area or volume regions at a desired hardening depth, which hardening depth typically extends into a previously solidified material, a relatively lower amount of energy or energy density is delivered in the boundary regions, thereby counter-balancing size inaccuracies caused by reflection and scattering phenomena in such boundary regions.

Hence, variation of energy density may be selectively controlled depending on whether area regions or boundary regions of a building region are exposed.

(vii) Viscosity and/or flowability of the material to be solidified:

The viscosity and/or flowability characteristics of the material to be solidified can be strongly affected by the presence of the filler substance in the material and may include, for example, liquid, fluid, thixotropic, semi-solid, paste, high-viscous, medium-viscous and low-viscous states. These states may vary depending on the status and point of time within the whole building process of a three-dimensional object, or may vary between different building areas or regions, or may vary between different first and second solidifyable materials used in a whole building process. For example, the actual viscosity and/or flowability existing in or at the building region, and/or in or at the object carrier, and/or in, at or near the solidifyable material carrier/provider may significantly differ, especially in or at a building region located between the object carrier (or the previously solidified material carried thereon) and the solidifyable material carrier/provider.

The present invention allows for an effective adaptation to each of such varying states by a corresponding preset adaptation or an in-situ control of the energy density.

(viii) Pressure and/or strain occurring in the actual building region during solidification of the material:

Observations similar to those under (vii) apply to the conditions of strain and/or contact pressure in or at the building region. These characteristics may be significantly affected by the presence of a filler substance in the material to be solidified. In particular, a condition selected from pressure, strain and material flowability becomes relevant in or at a building region located between the object carrier (or the previously solidified material carried thereon) and the solidifyable material carrier/provider. That is, a movement of the object carrier and/or the solidifyable material carrier/provider, either in a mutually vertical and/or horizontal manner, for providing the filler-containing solidifyable material at least in a building region will have a relevant influence on at least one of the afore mentioned conditions of pressure, strain and material flowability in, at or near the solidifyable material carrier/provider and/or in or at the building region and/or in or at the object carrier. A pressure or a strain being too high or too low, or a material flowability being too high or too low respectively in, at or near the solidifyable material carrier/provider and/or in or at the building region and/or in or at the object carrier may impair the building process.

Pre-setting and/or in-situ control of energy density depending on pressure and/or strain occurring in the actual building region during solidification of the filler-containing material thus provides an effective fine tuning of the freeform fabrication system.

In the performance of the present invention, a controlled variation of energy density for the aforementioned situations (i) to (viii) or for other situations can be determined and ascertained by theoretical considerations, or by practical experience. A practical testing or verification is preferred in cases where a fabrication system is adapted to the use of a yet unexperienced filler-containing material to be solidified. Hence, by testing one or more parameters discussed above, the effects of varied energy density and in particular a selective overexposure or underexposure in at least a part of an exposed pattern or image, or between patterns or images of different building regions, can be readily measured. This allows for a more accurate adjustment depending on the individual building parameters in the whole fabrication process, such as filler parameters, binder parameters, viscosity, flowability, desired selective hardening depth, and the respectively desired structure to be solidified as well as its surrounding structure.

The selective delivery of electromagnetic radiation and/or synergistic stimulation suitably includes an appropriate source capable of electromagnetic radiation and/or synergistic stimulation emission sufficient to solidify the material to be solidified. Solidification by electromagnetic radiation and/or synergistic stimulation according to the present invention may be understood as a process of solidification without photoreaction, such as gelation, fusion and/or sintering, but more preferably is understood as a process of gelation and/or solidification by photoreaction or by thermal setting reaction. Accordingly, the binder may be selected from the group consisting of inert binding agents; adhesives, which may gel and/or solidify without photoreaction or with photoreaction; and photopolymers or radiation sensitive resins, which may gel or solidify or cure by photoreaction and which normally include photopolymerization, cross-linking and/or network formation processes. Besides such a binder (first binder) being solidifyable or curable by the selective delivery of electromagnetic radiation and/or synergistic stimulation, a further binder (second binder) unaffected by such electromagnetic radiation and/or synergistic stimulation or affected by a electromagnetic radiation and/or synergistic stimulation but a modified one (e.g. at a different wavelength or intensity) may be used in addition.

The device for selective delivery of electromagnetic radiation and/or synergistic stimulation further preferably comprises a mask projector and/or a projection unit to deliver the electromagnetic radiation and/or synergistic stimulation selectively to the defined area or volume of material to be solidified. Electromagnetic radiation and/or synergistic stimulation can be delivered to the building region or parts thereof by means of further suitable components, including but not limited to optical elements, lenses, shutters, voxel matrix projectors, bitmap generators, mask projectors, mirrors and multi-mirror elements and the like. Examples of suitable radiation techniques to selectively deliver electromagnetic radiation and/or synergistic stimulation include, but are not limited to spatial light modulators (SLMs), projection units on the basis of Digital Light Processing (DLP®), DMD®, LCD, ILA®, LCOS, SXRD, etc., reflective and transmissive LCDs, LEDs or laser diodes emitted in lines or in a matrix, light valves, MEMs, laser systems, etc. Use of DLP mask projector is preferred.

Accordingly, in a particularly preferred embodiment of the present invention, there is independently provided a freeform fabrication system, which comprises: a material to be solidified, the material comprising a filler and a binder; a electromagnetic radiation and/or synergistic stimulation delivery device capable of delivering electromagnetic radiation and/or synergistic stimulation which allows an additive generation of a three-dimensional object by successive solidification of said material; and wherein said electromagnetic radiation and/or synergistic stimulation delivery device is based on a mask exposure system or a projection system. The above-mentioned devices having a mask unit and/or a projection unit are particularly suited for this embodiment by way of the selective delivering of electromagnetic radiation and/or synergistic stimulation. Such a freeform fabrication system is well suited and enables to perform the process according to the present invention in a rapid, efficient and reliable manner. Compared with other systems to produce three-dimensional objects, it produces objects actually having a high dimensional accuracy (relative to the nominal size desired); and it provides a high freedom in the desired design as well as in the selection of the materials both with respect to the filler and the binder matrix. Furthermore, this preferred freeform fabrication system provides a useful embodiment of its own: Independent from a variation of energy density, the energy density as such of the electromagnetic radiation and/or synergistic stimulation delivery device can be respectively set or controlled by a previous setting or by a control unit depending on at least one of the criteria:

(i) type, size and/or amount of filler contained in the material to be solidified;
(ii) type or amount of binder contained in the material to be solidified;
(iii) hardening depth;
(iv) presence or absence of underlying solidified, filler-containing material;
(v) size of the defined area or volume of said material to be solidified;
(vi) delivery of electromagnetic radiation and/or synergistic stimulation to area regions or to boundary regions of the three-dimensional object to be formed;
(vii) viscosity and/or flowability of the material to be solidified; and
(viii) pressure and/or strain occurring in the actual building region during solidification of the material.

Herein, the setting or the control parameters can be accomplished by a suitable pre-setting in advance of fabrication depending on the material to be used (in particular in case of (i) and (ii)) or depending on a desired built parameter ((in particular in case of (iii)), during a built program depending on the status or point of time of the whole procedure (in particular in any one case of (iii) to (vi)), or by in situ measurement and feedback-control (in particular in case of (viii) using e.g. a suitable sensor such as a flow measurement device, a pressure sensor or strain sensor). Suitable sensors are, for example, flowmeters, force sensors such as a piezo-electric device, a strain gauge, a differential pressure sensor, a touch sensor, a displacement sensor, or any other known or developed pressure or strain sensor.

The solidifiable material is subjected to selective delivery in a defined area or volume when placed in or on a suitable carrier or provider. Suitable examples for a solidifiable material carrier/provider to be used in the present invention include, but are not limited to a container or vat containing the solidifiable material, or a flexible and/or clear and/or resilient film/foil conveying the solidifiable material. When embodied as a film, the material may then be transferred by suitable film transfer techniques, before, during or after the solidification step. Larger volumes of solidifiable material may be stored and supplied from a reservoir or a solidifiable material cartridge to be conveyed to the solidifiable material provider.

Further, the growing and continuously or discontinuously built three-dimensional object may be carried on a suitable carrier or support. The object carrier/support is normally movably arranged in the fabrication system to allow a spatially controlled relationship with the material to be solidified. Alternatively or in combination therewith, the solidifiable material carrier/provider may be arranged movably in a spatially controlled relationship with the object carrier/support (and thus with previously solidified object). Various modifications are feasible when applying the principle of the present invention.

The source for delivery of electromagnetic radiation and/or synergistic stimulation and further optical elements as described above can be arranged relative to the material to be solidified as well as its provider and/or carrier in various suitable ways. For example, the arrangement may be such that electromagnetic radiation and/or synergistic stimulation is delivered from above the building region or the solidifiable material carrier/provider (in which case a carrier for carrying the produced three-dimensional object is usually placed below the building region or a solidifiable material carrier/provider), or one where electromagnetic radiation and/or synergistic stimulation is delivered from below the building region or a solidifiable material carrier/provider (in which case the carrier for carrying the produced three-dimensional object is usually placed above the building region or a solidifiable material carrier/provider). Again, various modifications are feasible.

A building region may be formed, for example, by a building plane/area or a building volume with desired dimensions in X, Y and Z directions (including, for example, XY plane and areas, XZ plane and areas, and YZ plane and areas as well as any X, Y, Z volumes). A building area may be flat, but is not necessarily flat. Further, building regions may be formed as layers, as cross-sections, as a matrix such as a point matrix, a line matrix and especially a voxel matrix, or in any other forms. A desired three-dimensional object can eventually be formed by an additive generative process involving successive solidification of the material in respective building regions.

According to the present invention, energy density can be delivered to the exposure pattern or image, and/or patterns or images of different building regions of the material to be solidified, in various ways or means. To make a variation of energy density efficient and controllable, the selective delivery of electromagnetic radiation and/or synergistic stimulation is preferably based on an imaging unit comprising a predetermined number of discrete imaging elements or pixels, and the variation of energy density is performed by controlling the discrete imaging elements or pixels in a selective manner. A preferred exposure system being advantageous for the varied energy density exposure is the use of a voxel matrix, which is defined according to the invention as a rastered arrangement of solidified voxels (volume pixels), wherein a voxel images an image point of a pixel matrix, and the hardening depth per voxel depends on the energy input per image point. The afore-mentioned exposure systems are particularly suitable for the freeform fabrication method of stereolithography.

According to the present invention, energy density of the electromagnetic radiation and/or synergistic stimulation can be varied by suitable ways or means. Particularly preferred ways or means include, alone or in combination, the following:

(a) Various exposure times within the dimensions of XY, XZ, YZ or in Z direction of one or more building regions. For example, this can also be accomplished by using selective shutters with appropriate timings, or selective mask exposures.

(b) Number of multiple exposures of at least parts of a pattern or an image, or of a pattern or image of at least one among different building regions. For example, this can be performed by applying multiple mask exposures of a certain cross-sectional area or other building regions of the three-dimensional object to be formed, wherein parts of the respective multiple masks preferably overlap for overexposure of the selected area or region.

(c) Gradation of energy density in one or more parts of the exposed pattern or image or between patterns or images of different building regions.

This can be most efficiently performed by allocating certain grey values or color values to corresponding parts of a pattern or image, or to one among the plurality of building regions. The parts allocated by grey or color values are correspondingly underexposed relative to full bright values, yet overexposed relative to black values. Grey value or color value allocation is most efficiently made pixel-wise in a pixel matrix or a voxel matrix system. Since gradation of energy density combines ease of processing with the achievement of high accuracy in the use of filler-containing materials to be solidified, this embodiment is preferably applied, alone or in combination with other variation means.

(d) Location of focal plane or focal point within the building region.

Normally, the focal plane or focal point, in particular in systems using a mask exposure or a projector unit for the selective delivery to a defined area or volume of the material to be solidified, coincides with the surface of the material to be solidified. However, modifying this normal arrangement such that the focal plane or focal point of the applied optical system is spaced apart from this surface, i.e. is actively changed to be located at a certain depth below this surface will—relative to an unmodified/unvaried normal system—underexpose the surface and overexpose corresponding depth regions in order to counter-balance higher energy absorption rates of the composite material and especially the filler substance in the surface region.

(e) Applying a second source or a second delivery of electromagnetic and/or synergistic radiation. For example, the second source or second delivery of electromagnetic radiation and/or synergistic stimulation may be accomplished by a dual or multiple illumination system including the use of two or more radiation sources having respectively same or different wavelengths. In this embodiment, the second or further illumination source may be directed selectively to those parts of a pattern or image, or to that building region among other building regions that need to be overexposed at a desired spatial location as explained above. Alternatively, a general infrared (IR) heating source may be used for the general delivery of a basic energy density, while a specific source for delivering electromagnetic radiation and/or synergistic stimulation active for solidifying the material is applied selectively to those parts within a pattern or image, or to that building region among other building regions that need to be exposed by additional energy density. The first and the second or further sources or deliveries of electromagnetic radiation and/or synergistic stimulation may be located on the same side or on different sides relatively to the building region(s). Further, the deliveries of first and second or further electromagnetic and/or synergistic radiations may be respectively oriented in the same direction or in different directions.

Any variations or combinations of the above variation embodiments are possible and feasible for a person skilled in the art.

The filler to be mixed with a binder for providing a material to be solidified according to the present invention typically is a solid or substantially solid substance and may include, without being limited to: a ceramic substance such as e.g. alumina, magnesia, zirconia, ceramic oxides of other transition metals such as titania, hafnium oxide, rare earth metal oxides, spinel type double metal oxide ceramics, or mixtures thereof; cermets; silicate, aluminosilicate, apatite, fluoroapatite, hydroxylapatite, phosphates such as tricalcium phosphate, calcium magnesium phosphate, calcium ammonium phosphate, mullite, spinels, and mixtures thereof; glass materials, such as silicate glass, borsilicate glass, quartz glass and mixtures thereof; metals and metal alloys such as stainless steel, titanium or titanium alloy, nickel alloy, copper or copper alloy such as brass (70% copper and 30% zinc), aluminium or aluminium alloy, iron or iron alloy and mixtures thereof; solid polymers or polymer blends such as polymerized acrylic resins and blends or copolymers thereof like polyurethane/polyacrylates, acrylonitril/butadien/styrene-polymerisates (ABS), epoxides and copolymers thereof, nylon and blends or copolymers thereof, polyamide elatomers and mixtures thereof, and other filler substances. In a preferred embodiment, which is particularly beneficial for dental applications in terms of achieving high mechanical strength at good homogeneity combined with high size accuracy (especially when the process includes post-treatment such as sintering and thereby a transformation from a first to a second circumferential size), the filler substance is a ceramic powder, preferably a powder comprising ceramic materials selected from alumina, zirconia, or a mixture thereof. A particularly preferred ceramic powder comprises a ceramic material selected from monoclinical or non-monoclinical zirconia, yttria-doped or -stabilized tetragonal monoclinical or non-monoclinical, single or non-single phased zirkonia (i.e. $ZrO_2$ containing 3-5 mol-% $Y_2O_3$), especially 3YTZP.

The filler component may further comprise one or more kinds of additives, for example but not limited to dispersants, coloring agents such as pigments, post-treatment auxiliary additives such as sintering aids or stabilizers, etc.

The filler may co-fuse or co-sinter itself under the action of electromagnetic radiation and/or synergistic stimulation used for solidification (e.g. especially when polymer fillers are used). It is on the other hand preferred that the filler itself is inert with respect electromagnetic radiation and/or synergistic stimulation at a level which solidifies the binder admixed with the filler, but may nevertheless co-fuse or co-sinter in a post-treatment described later (e.g. when ceramics, glass or metals/metal alloys are used).

The filler may be in the form of particles, a powder, fibers, a net, a scaffold, and the like. The particularly preferred particulate form of the filler is a powder having a suitable particle size, preferably being spherical or essentially spherical in shape, and further preferably having a mean particle size in a range of about 0.001 µm to 100 µm, more preferably in a range of about 0.01 to 50 µm and particularly in a range of about 0.1 to 10 µm. As to the distribution of the absolute particle size of the filler, it may range from about 1 nm to 1000 µm or higher, more preferably from about 0.1 µm to 100 µm. The filler may have a monomodal, a bimodal or a trimodal size distribution, using the same or different filler materials.

The binder substance for the material to be solidified according to the present invention is suitably selected from substances which may themselves lead to solidification of the composite material upon exposure to electromagnetic and/or synergistic radiation. A thus selected binder may not necessarily solidify through photoreaction, but through other mechanisms such as gelation, or it may solidify by chemical reaction after activation through electromagnetic and/or synergistic radiation, possibly together with other co-reactants. Suitable examples of this type of binder are adhesives, including but not limited to waxes and modified waxes, thermally setting resins such as epoxides, and the like. The adhesive properties of adhesives can may be exerted not before solidification of the material to be solidified, and thereby allows partial structures such as layers, strands, dots or other structures or scaffolds, which contain a particulate or fibrous filler, to be successively attached together and to thereby build the three-dimensional object, even without performing a photocuring reaction.

According to a preferred embodiment, the binder contains at least one selected from photopolymers and thermally hardened resins, in particular a photopolymer which is hardened when subjected to electromagnetic radiation and/or synergistic stimulation of interest. Accordingly, a photopolymer to be used as a binder material may include, but is not limited to: acrylate and/or methacrylate containing compounds, for example mono-, di-, tri-, tetra-, pentaacrylate, such as alkyl- or alkoxy-(meth)acrylates, (meth)acrylic esters having short or long chain alkyl ester groups, e.g. alkyl glycol di(meth) acrylate; epoxy group containing compounds; vinyl group containing or vinyl ether group containing compounds; polysiloxanes; and the like, as well as mixtures thereof. Alternatively, a thermal hardening polymer substance such as an epoxy group containing compound may be used, which is preferably protected with an amine group that decomposes in response to light and/or heat.

The composite material to be solidified according to the present invention may contain further auxiliary agents, including but not limited to: photoinitiators, which may be selected depending on the desired wavelength of electromagnetic and/or synergistic radiation, such as 2-benzyl-2-dimethylamino-1(4-morpholino phenyl)butanone, 1,2,2'-dimethoxy-2-phenylacetophenol, bisimidazoles, benzophenones, α-aminoketones, xanthenes, fluorenes, fluorones, ferrocenes, and the like; co-initiators and/or activation agents such as thioxanthones (e.g. isopropyl thioxanthone1-chloro-4-propoxythioxanthone), 4-benzoyl-4'-methyldiphenyl sulfide, ethyl-p-dimethylaminobenzoate, N,N-dialkyltoluidine or -aniline, benzophenones, diaryliodo compounds, borates, phosphites, and the like; rheology adjusting agents; viscosity adjusting agents; diluents; solvents; colorants such as dyes and/or color pigments; thixotropic agents; thickeners; stabilizers; coupling agents; welting agents; dispersants; lubricants; adhesives; pore forming agents; and the like, respectively alone or in combination.

The material to be solidified may be provided in a suitable form, including but not limited to liquid, fluid, thixotropic, semi-solid, paste, high-viscous, medium-viscous and low-viscous materials. Preferably but in no way limiting, it has viscosity in the range of about 0.1 Pa·s to $5\times10^3$ Pa·s, preferably about 0.2 to about $1\times10^3$ Pa·s, more preferably 1 Pa·s to 200 Pa·s, and in particular 10 Pa·s to 100 Pa·s, respectively measured at 25° C.

A suitable content of the filler substance in the whole material to be solidified lies in a range of about 0.5% by weight to 99.9% by weight, preferably about 1% by weight to about 99% by weight, and more preferably 10% by weight to 85% by weight, particularly above 50% by weight to 85% by weight, and still further preferred 70% by weight to 80% by weight.

After solidification, the three-dimensional object thus produced may be subjected to one or more post-treatments. Suitable post-treatments are selected from post-hardening, de-binding, fusing and sintering, alone or in combination. Post-hardening may be performed by a general exposure to an appropriate electromagnetic and/or synergistic radiation, such as microwave irradiation. A suitable de-binding process for removing or substantially removing binder or another component of the composite material other than the filler substance may be performed by suitable thermal treatment, for example in a range of at least 200° C., for example from 200° C. to 600° C., possibly under normal atmosphere, under inert gas atmosphere, and/or under vacuum. Fusing and/or sintering may be performed at a temperature adjusted to the respective filler substance used, suitably at temperatures below the melting point of the filler material. For example with metal or metal alloy fillers, sintering may be performed at a temperature between about 1,050° C. and 1,450° C., especially between about 1,150° C. and 1,300° C., and ceramic filler materials may be sintered at a temperature of between about 900° C. to about 1,850° C. depending on particle size distribution of the powder used initially as a filler and/or the desired density of the final sintered product, more specifically about 900° C. and 1,700° C. The temperature treatment scheme may include a controlled heat-up speed, for example in a range of 0.1 to 10° C./min, more preferably 0.2° C. to 2° C./min while holding the object for a longer period in the afore-mentioned temperature ranges, as well as an appropriate cooling speed as desired. After-treatments of de-binding and sintering may be performed individually in different steps, continuously or discontinuously one after another, or in any combination, while selecting appropriate temperatures and timings.

A preferred system according to the present invention comprises a freeform fabrication system using a mask exposure system or a projection system for the delivery of electromagnetic radiation and/or synergistic stimulation, whereupon after solidification, the obtained three-dimensional object is subjected to sintering in order to obtain the desired final three-dimensional size. After the additive or generative process including all solidification for obtaining a three-dimensional object having a first circumferential size in an untreated state, post-treatment may well lead to a second, normally smaller circumferential size, in particular in a sintered state. This embodiment is advantageously applied in particular when the material to be solidified comprises a ceramic filler besides the binder.

The present invention allows for obtaining a freeform three-dimensional object on the basis of the afore-defined composite material comprising filler and binder, such that the resulting object may have an excellent homogeneous mechanical strength. Accordingly, it may be possible to homogenize mechanical strength within the three-dimensional object formed by a freeform fabrication system with an intra-object standard deviation of maximally 10% or lower, preferably maximally 5% or lower, more preferably maximally 2% or lower, and even 1% or lower which is determined by measuring a mechanical strength property (typically flexural strength) at multiple points within the formed object, preferably at least 5 points and typically at 10 points, and determining the standard deviation with respect the mean value to the measured points. A particular characteristic of the present invention is that the afore-mentioned homogeneous mechanical strength is obtainable at a high level in a unique combination with an opposite trade-off property, namely dimensional accuracy. Thereby, it is possible to combine the afore-mentioned homogeneous mechanical strength at high level with a dimensional accuracy of maximally 5%, more preferably maximally 2%, still more preferably maximally 1% and in particular maximally 0.5% relative to the nominal dimensional size (such as length, width, diagonal or the like) of a model used for designing the three-dimensional object. Hence, it will be possible according to the present invention to make a compromise between trade-off properties caused by spatially distinct absorption/reflection/scattering phenomena based on the filler substance, and shrinkage and especially differential shrinkage phenomena predominantly caused by the binder, each phenomenon isotropically or anisotropically affecting counter-acting distortions or deformations within the solidified three-dimensional object. The advantageous properties and combinations of properties achieved by the present invention with the solidified three-dimensional object will be transformed into a final three-dimensional object after optional post-treatments such as post-hardening, de-binding, fusing and/or sintering.

Therefore, a finally sintered three-dimensional object may be realized according to the present invention, which may have an absolute dimensional accuracy, relative to the originally desired nominal circumferential size, of ±100 µm or below, more advantageously in the range of ±5 to 50 µm and even of ±5 µm or below. At the same time, it may be realized to obtain an extremely high sinter density, defined e.g. by a total porosity, which would include open and closed pores, of lower than 2%, preferably lower than 1% and particularly lower than 0.2% and even close to 0%. Compared with conventional techniques of producing three-dimensional bulk objects other than freeform fabrication, and especially compared with such conventional objects having been sintered which finally have to undergo a milling process and optionally a high-density pressurizing process, the freeform (i.e. additive/generative) 3D object fabrication system and thus the eventually sintered 3D objects according to the present invention can avoid such milling and high-density pressurizing process steps and therefore do not have structural drawbacks associated therewith such as surface defects and crack formations.

The freeform fabrication system has particular advantages when applying stereolithography systems, and accordingly the freeform three-dimensional object is preferably obtained by a stereolithography process. The freeform fabrication system may be performed in layers, in other cross-sectional building structures, in a voxel-based building structure, continuously or discontinuously, or any combination thereof. It is thus a particular advantage that a layer-wise formation is not necessarily required, which further improves fabrication freedom. The freeform fabrication and preferably stereolithography fabrication system is preferably applied to the fabrication of three-dimensional objects comprising, in the building direction of the material, multiple portions having respectively different sectional areas, and if desired it is preferably applied to a multitude of three-dimensional objects or any other complex building structure with respectively different building regions. This includes complex structures involving purposive three-dimensional object parts besides auxiliary support structures. It is a particular advantage of the present invention that different building structures, or a building structure besides auxiliary support structures, can thus be formed partially without a filler, or with another composite material containing a different type and/or amount of filler substance.

Due to the advantageous characteristics described above, the present invention is particularly suited for designing the freeform three-dimensional object as a medical product, such as an implant, an artificial tissue, a bone filler or a bone substitute, and in particular a dental product. Suitable dental products include, but are not limited to a filling, a restoration, a crown, a veneer, a prosthetic, an inlay, an onlay, tooth denture, attachments, artificial teeth, or the like. The dental product is typically a sintered material. The sintered material may be provided with an additional glaze, sintered ceramic and/or glass-ceramic layer.

BRIEF DESCRIPTION OF THE DRAWINGS

The present invention will be described in more detail by referring to preferred embodiments, examples and figures, which are however for illustrative purposes only and shall not be understood in a limiting manner, wherein.

DETAILED DESCRIPTION

Figure 1:
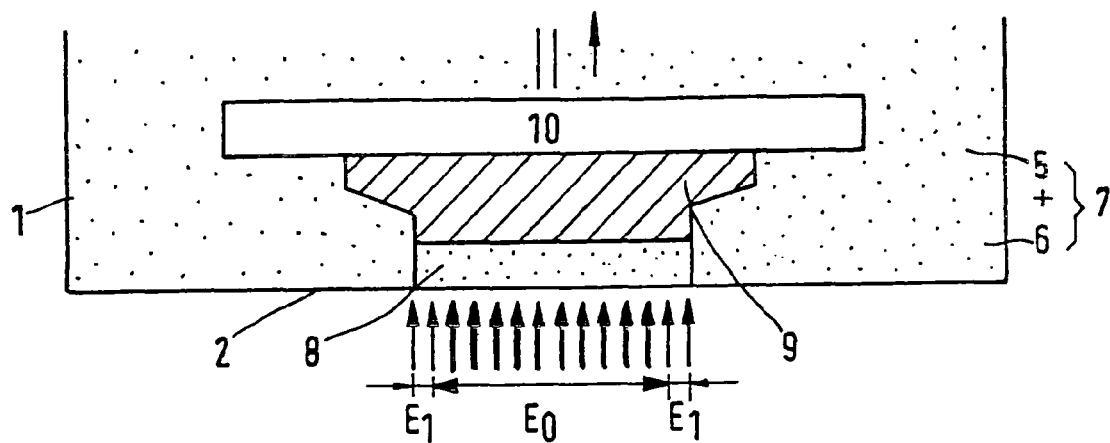
FIG. 1 schematically shows a principle of the present invention by referring to a particular embodiment of a freeform fabrication system where energy density of electromagnetic radiation and/or synergistic stimulation is varied within a pattern or image in XY plane.

According to FIG. 1, in a particular embodiment of a process and a system of freeform fabrication for producing a three-dimensional object based on stereolithography technique, there is used a container or vat 1 for providing a material 7 to be solidified, the material 7 comprising a particulate filler 6 such as yttria stabilized tetragonal zirkonia phase (3YTZP) and a binder 5 such as an acrylate resin. The material 7 to be solidified may contain further constituents as described above, such as a sintering aid in the filler substance and a photoinitiator in the binder, and optionally further auxiliary agents. FIG. 1 shows a process and a system at a certain moment during performance, where a part 9 of a desired three-dimensional object has already been produced and is carried on a three-dimensional object carrier/provider 10, illustrated here in the form of a platform. A gap is formed between the surface of previously solidified partial object 9 and a bottom 2 of the container or vat 1 by an upward movement of three-dimensional object carrier/support 10 (indicated by an arrow at three-dimensional object carrier/support stem). By this upward movement, material yet to be solidified fills the gap, such that the material 7 to be solidified is provided in a desired building region 8. The bottom 2 of vat or container 1 is transparent or transmissive to electromagnetic radiation and/or synergistic stimulation to be used for solidification, at least in a functional part of the bottom.

Within an area defined by XY or a corresponding volume extending in Z direction to thereby specifically define the desired building region 8, electromagnetic radiation and/or synergistic stimulation is selectively delivered as indicated by parallel arrows from below the bottom 2 of vat 1. Here, an exposed energy density is varied in boundary regions of a corresponding exposure pattern such that, based on a prevailing reflecting and scattering nature of a metal powder filler as filler substance 6, exposure energy density $E_1$ in the boundary region is lower than energy density $E_0$ applied in the inner area region. Variation of energy density can be effected by allocating grey level to the boundary regions of a mask exposure system, relative to an ungraded, bright exposure level of the mask in the inner area region.

Conversely, modifying the fabrication system by using a prevailing absorbing filler substance, energy density variation can be modified in a different manner (not shown) such that higher energy density ($E_1'$) can be exposed in boundary regions, whereas relatively lower basic energy density ($E_0'$) can be exposed to the remaining inner area except the boundary margins.

In this manner, the freeform fabrication system can be adapted and adjusted to the use of a particular filler substance. Moreover, given a predetermined system, accuracy, shrinkage control and homogeneous mechanical strength can be significantly improved by the differential control with respect to boundary regions and large structural area regions, respectively.

Figure 2:
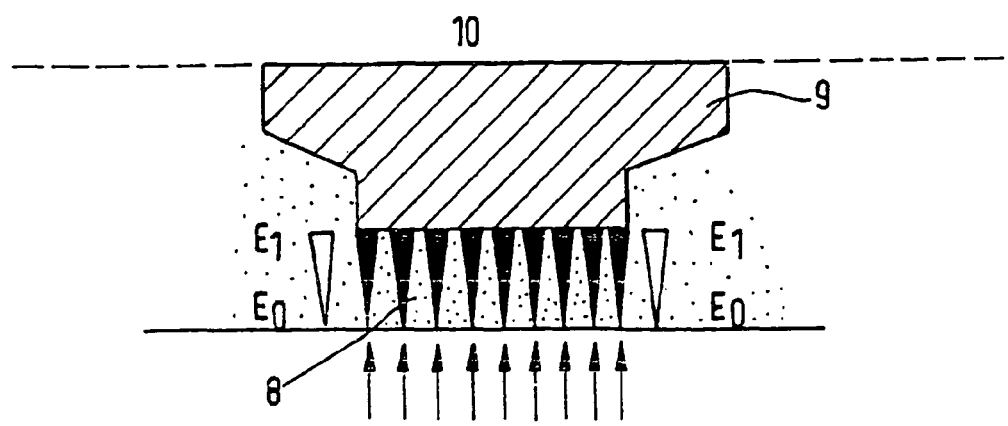
FIG. 2 schematically shows a principle of the present invention by another particular embodiment of a freeform fabrication system where energy density of electromagnetic radiation and/or synergistic stimulation is varied in Z direction of an exposure pattern extending in XY plane.
Figure 3:
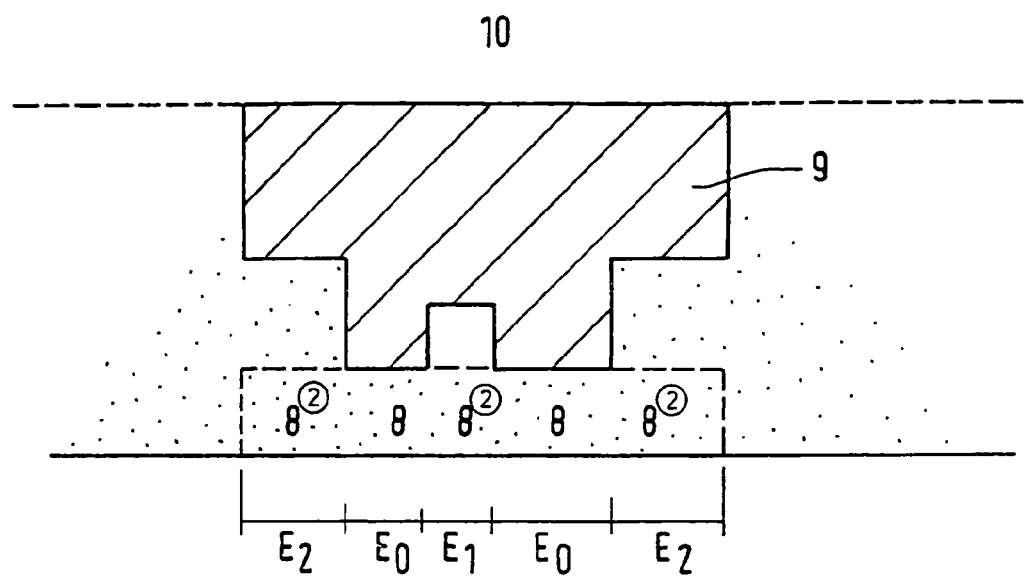
FIG. 3 schematically shows a principle of the present invention in a particular embodiment employing variation of energy density depending on special locations within a building region, i.e. whether an overhanging structure, or a structure over-/underlying a previously solidified material, or above/under a hollow cavity shall be solidified.

FIGS. 2 and 3 show alternative embodiments or modifications of the fabrication system of FIG. 1 and further illustrate a principle of the present invention. While the relevant portion including the specifically selected and defined area or volume of the material to be solidified in a desired building region is illustrated both in FIG. 2 and FIG. 3, other components and conditions may be the same as shown in FIG. 1.

According to FIG. 2, a variation of energy density is applied, where energy density is unusually increased from a surface where electromagnetic radiation and/or synergistic stimulation impinges on the material to be solidified towards a surface of previously solidified three-dimensional object 9, i.e. in the Z irradiation direction within building region 8 formed in the gap. This is illustrated in FIG. 2 by a gradually increasing energy density from $E_0$ to $E_1$. Thus, contrary to an unmodified system where a decrease of energy density from $E_0$ to $E_1$ would be enhanced by the presence of a filler substance, an unusual variation in energy density in building direction Z (i.e. throughout the exposed XY plane) is applied. This may be accomplished by shifting the focal plane of the exposure pattern or image away from solidification surface 2 (at the bottom plane 2) in Z direction, e.g. to a location at the previously solidified surface of object 9 (i.e. coinciding with the gap distance determined by the Z dimension of building region 8), or alternatively at a smaller or larger distance. Another means to accomplish this, alternatively or in addition, is superimposing another electromagnetic radiation and/ or synergistic stimulation field emitted from the opposite side, possibly in a field directed towards the building region only (not shown). A sum of the electromagnetic radiation and/or synergistic stimulation fields thereby increases from $E_0$ to $E_1$. For this purpose, an infrared (IR) radiation for emitting and delivering thermal energy from the upper side of FIG. 2 may be used for example. For example, an IR emitter may be incorporated into the three-dimensional object carrier/support 10, and preferably being selectively controllable within the XY plane for selective super-exposure in a desired building region.

According to FIG. 3, variation of energy density exposure is performed depending on which sectional part of the building region is concerned. Here, in the particular embodiment illustrated, a basic energy density $E_0$ is used in portion(s) of the exposure pattern allocated to the part of building region 8 where an over-/underlying previously solidified material 9 is present, whereas modified energy densities $E_1$ and $E_2$ are allocated to portions of building regions $8^{①}$ and $8^{②}$ referring to cavity portions or overhang portions, respectively.

Using a solidifying material comprising a reflecting and/or scattering filler substance, the system may be adjusted in a manner that $E_0$ is higher than each of $E_1$ and $E_2$. Further, a condition of $E_1 \geqq E_2$ may be set.

Figure 4:
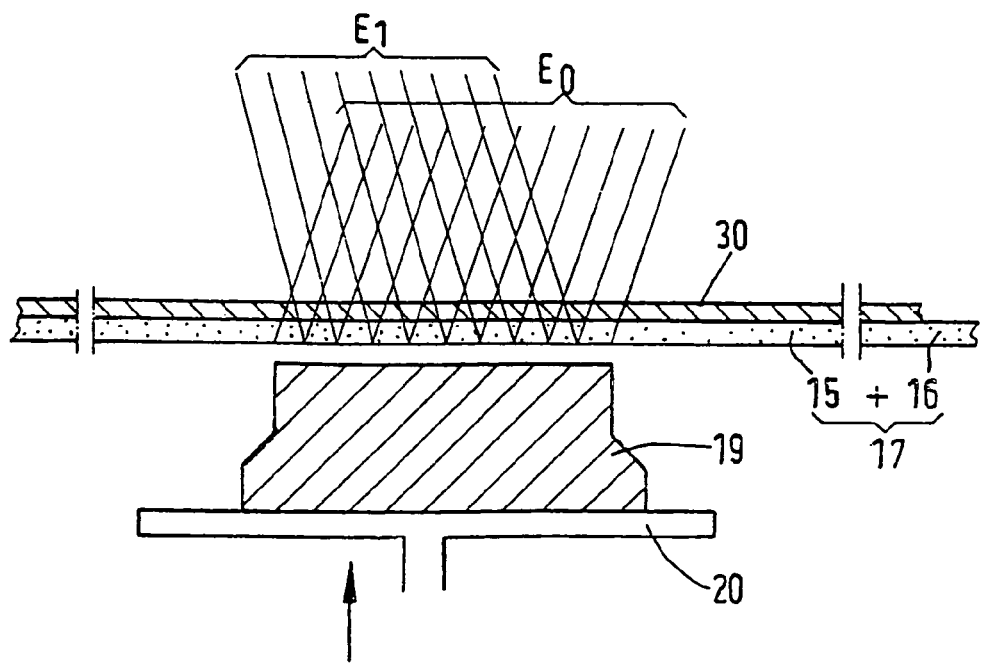
FIG. 4 schematically shows a principle of the present invention using a freeform fabrication system on the basis of a transparent film that carries material to be solidified according to another embodiment, and wherein varied energy density is achieved by superimposing electromagnetic and/or synergistic radiations from different delivery sources.
Figure 5A:
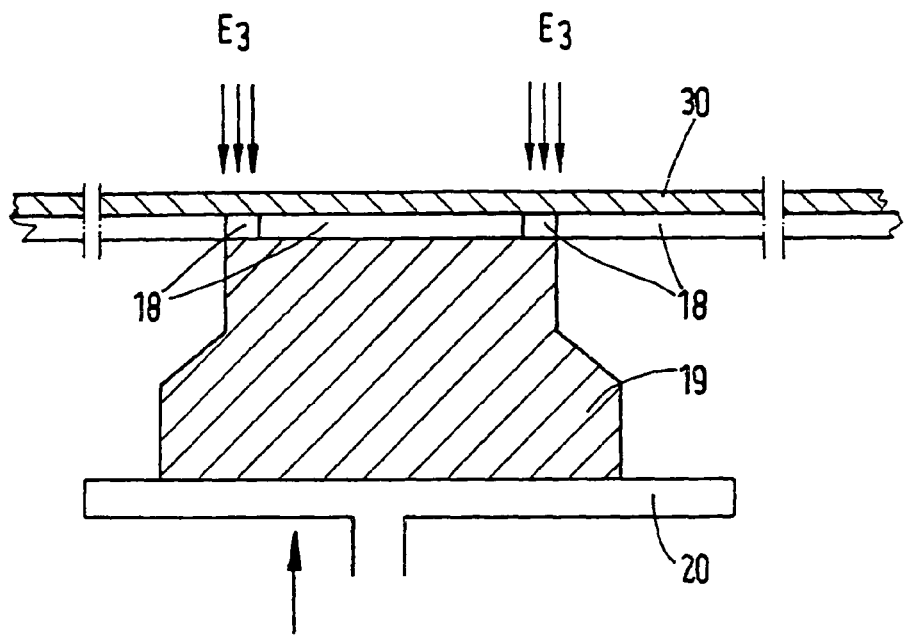
FIGS. 5A and 5B schematically show a principle of the present invention according to another embodiment, wherein different building regions are formed by varied energy densities, respectively, involving building region(s) with a first, filler-containing material to be solidified and one or more other building region using a second, different material to be solidified, wherein the different building regions are associated with correspondingly different energy densities.
Figure 5B:
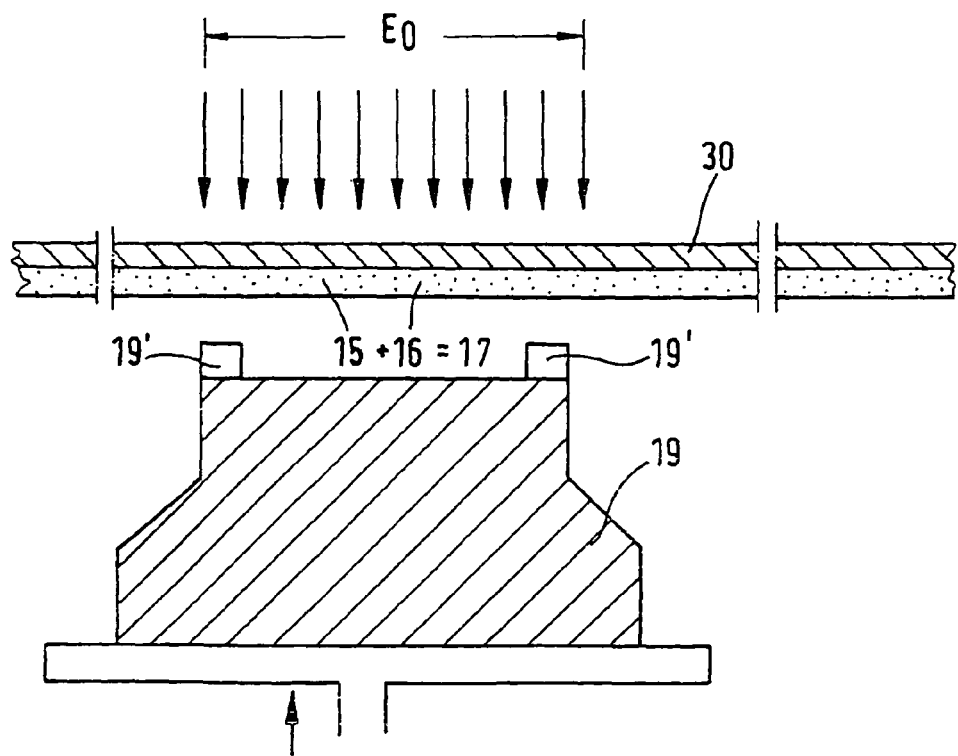

In further embodiments illustrated in FIGS. 4 and 5A and 5B, variations of a freeform fabrication system and process based on film transfer imaging technology are used for applying a principle of the present invention. In these embodiments, a belt 30, which may be provided in the form of an endless belt, is made of a transparent and/or flexible and/or resilient rubber/film/foil to provide thereon material 17 to be solidified. Material 17 to be solidified again contains filler substance 16 and a binder 15 and optionally further constituents as described above. The figures show certain stages within the entire fabrication process, where a part 19 of the final three-dimensional object had already been formed and placed on three-dimensional object carrier/support 20 embodied as a build platform. When a further layer of material shall be placed on top of object part 19, it is moved by an upward movement of carrier/support 20 to get in contact with the material 17 yet to be solidified. Once a contact is reached, electromagnetic radiation and/or synergistic stimulation is delivered in a pattern or an image with an associated basic energy density $E_0$ within the defined area of a building region (in this case a further layer to be solidified).

According to the embodiment illustrated by FIG. 4, energy density is varied by the super-exposure using an additional, second source of electromagnetic radiation and/or synergistic stimulation delivering or supplying further energy density $E_1$ in a desired part of the exposure pattern or image. Here, as a ceramic filler substance may be included into the material together with a binder substance, super-exposure with $E_1+E_0$ is carried out in an inner area region of the layer to be formed, relative to basic energy density $E_0$ remaining in boundary regions, in order to counter-act inhomogeneities caused by scattering phenomena in boundary regions. First electromagnetic radiation and/or synergistic stimulation associated with $E_0$ and second electromagnetic radiation and/or synergistic stimulation associated with $E_1$ may have same or different wavelengths.

In another embodiment as illustrated by FIGS. 5A and 5B, a principle of the present invention is explained when different building regions or different layers are used, or alternatively when different first and second materials are used for one or more building regions. In a particularly exemplified step illustrated by FIG. 5A, a modified second material 18 having no filler substance or another filler substance, different from the compositions 15, 16 or 17 of FIG. 4 described above, had been applied for forming a delicate structural portion, for example a modified structure or an auxiliary support structure, at a building region by exposure to electromagnetic radiation and/or synergistic stimulation associated with energy density $E_3$ only. After separation from belt 30, this belt 30 or another belt carrying again the first material 17 to be solidified and containing filler 16 and binder 15 is supplied. Upon a further contact by redirecting partial object (structure 19 plus 19') with a movement of its carrier/support 20 upwards and towards material 17, basic energy density $E_0$ varied relative to $E_3$ is exposed for the next building region or next layer for forming another part of the three-dimensional object. Alternatively, instead of using different first and second materials 17 and 18 to be solidified, respectively, varied energy densities $E_3$ and $E_0$ may nevertheless be applied advantageously even with using the same materials to be solidified, the variation however being performed due to the quite different building region structure (delicate structure 19' and overlying layer formed over the whole cross-section of object 19).

Figure 6:
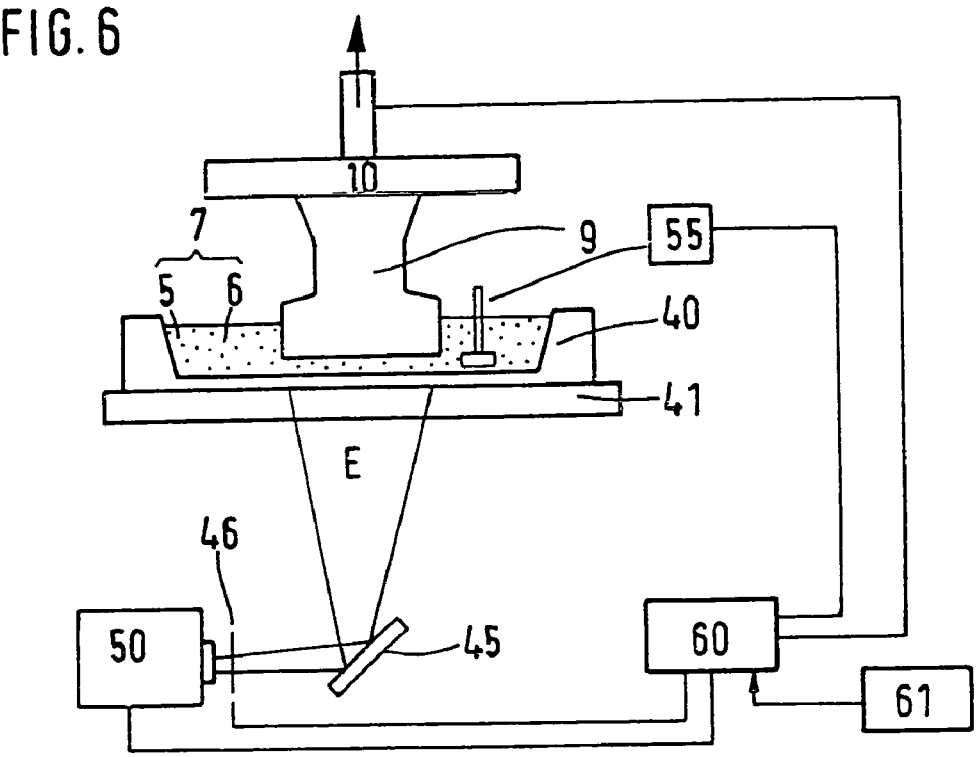
FIG. 6 schematically shows another embodiment of the present invention using a freeform fabrication system with a projection unit for selectively delivering electromagnetic radiation and/or synergistic stimulation, wherein energy density of is appropriately preset or adjusted depending on constitution and or characteristics of a material to be solidified containing a filler and a binder.
Figure 7:
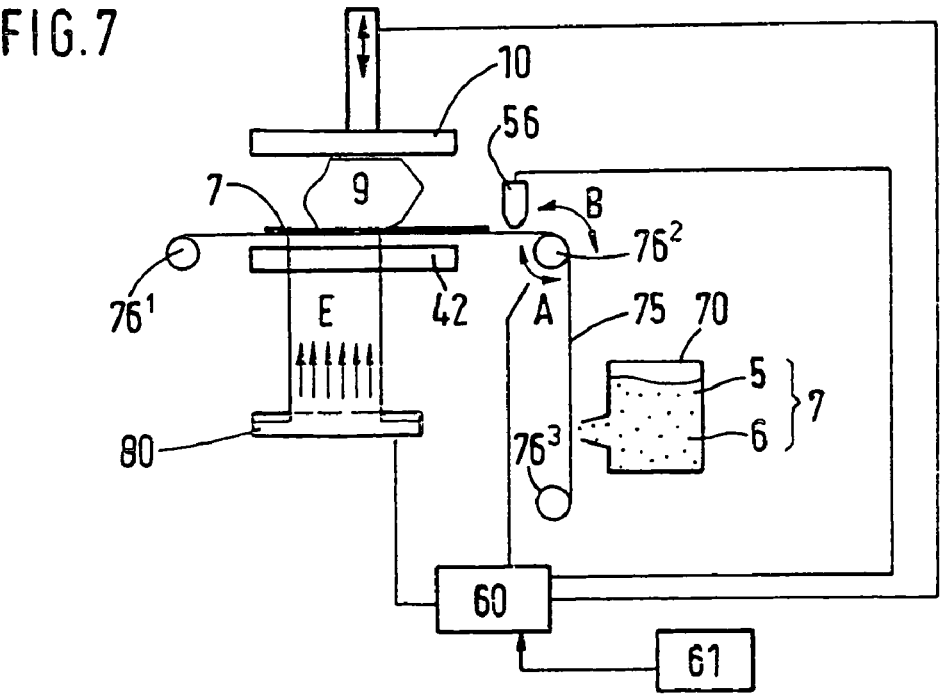
FIG. 7 schematically shows still another embodiment of the present invention using a freeform fabrication system using a film transfer technique and using a mask exposure unit for selectively delivering electromagnetic radiation and/or synergistic stimulation, wherein similar to the embodiment of FIG. 6 energy density of is appropriately preset or adjusted depending on constitution and or characteristics of a material to be solidified containing a filler and a binder.

In the embodiments schematically illustrated by FIGS. 6 and 7, it is not necessary but still possible to vary energy density as described in the previous embodiments within the pattern or image and/or between patterns or images of different building regions of the same or different materials. However, in these embodiments useful of its own, the energy density of the electromagnetic radiation and/or synergistic stimulation delivery device as such can be respectively set or controlled by a previous setting or by a suitable control unit depending on at least one of the criteria (i) to (viii) mentioned above.

The embodiment shown in FIG. 6 again uses a material 7 to be solidified which contains at least binder 5 and filler 6 and which is contained in a vat, container or trough 40. The bottom of vat/container/trough 40 and a glass or plastic plate 41 used for its support is transparent to the type of electromagnetic radiation used. In this embodiment, electromagnetic radiation is projected from a projection unit 50 through a shutter 46 and via a reflector 45 to form a desired exposure image in or at the building region, to thereby solidify material 7 and to bind it to part 9 previously formed on the three-dimensional object carrier/support 10, which is again embodied as a build platform. In this manner a desired three-dimensional object can be successively formed either continuously or discontinuously, for example layer-wise with intermediate layer separations or in a suitable voxel matrix. A control unit embodied by a computer unit 60 serves to control operations of the freeform fabrication system at suitable locations, e.g. the projection unit 50 for tuning energy density E, the shutter 45 for opening and closing the path of the electromagnetic radiation, and the three-dimensional object carrier/support 10 for its movement (e.g. upward as indicated by an arrow) for enabling delivery of fresh material to be solidified. Here, the energy density E of the projection and exposure unit can be manually preset and input by a suitable control module 61 in advance of the building process, for example depending on the material used and known before (i.e. according to any one or a combination of parameters (i) and (ii) described above, such as type, particle size or amount of filler; type or amount of binder). Alternatively or in addition, energy density E can be manually set and input into the control module 61, or is adjusted in-situ during the built program and built process depending on any one or a combination of parameters (iii) to (viii) described above.

As a further possible option, a flowmeter or a viscosity meter (indicated by reference sign 55) may be provided if desired, allowing to measure in advance for a presetting operation, or to measure in situ during the building process either flowability or viscosity or both, in order to control the energy density E delivered by the projection unit 50 via control unit 60.

As a still further possible option, the energy density E delivered by the projector may be varied, if desired, in the exposed area of the building region, in order to further counteract scattering, reflection and/or absorption phenomena by the filler 6, as basically explained in the previous embodiments (i.e. by delivering spatially distinct energy densities $E_0$, $E_1$, etc.).

The embodiment shown in FIG. 7 illustrates a modification of the above embodiments for film transfer imaging techniques. Here, a embodiment of a freeform fabrication system according to the present invention uses a flexible and/or clear and/or resilient film/foil (respectively denoted by reference sign 75) conveying the material to be solidified 7 which again contains at least binder 5 and filler 6. The film 75, which is here transparent to the electromagnetic radiation of interest at least in the built area, is adapted to transport material 7 to be solidified, which is dispensed from a solidifying material reservoir 70 onto one side of the film, from a supply station to the built area, to be subjected to radiation action in the desired building region through delivery of a prescribed energy density E. Transport may be carried out by an active roller $76^2$ under the control of control unit 60, while other rollers $76^1$ and $76^3$ may be passive and merely roll up remaining ends of flexible film 75. Further provided is a transparent glass or plastic plate 42 for providing support for flexible film 75 carrying the material 7 at the built area. This enhances the provision of a planar reference plane when desirable.

In this embodiment, the electromagnetic radiation and/or synergistic stimulation device is embodied by a mask exposure system comprising a bitmap generator and mask projector (commonly referred to by reference sign 80). By the mask exposure system (and optionally a further energy source not shown), energy density E is delivered selectively to the desired area of the building region in or at the reference plane. A control unit 60 is arranged to control the mask exposure system 80 for tuning energy density E, and may further control the whole system at suitable other locations, such as at the three-dimensional object carrier/support 10 for its movement (e.g. upward and downward as indicated by a double arrow) to enable steps of contacting fresh material 7 and of separation after solidification, at the opening of solidifying material reservoir 70 for the controlled dispensing of a fresh material film 7, etc. Similar to the embodiment of FIG. 6, the energy density E of the mask exposure system can be manually preset and input by a suitable control module 61 in advance of the building process, or alternatively or in addition, it can be adjusted in-situ during the built program and built process depending on any one or a combination of parameters (i) to (viii) described above.

In the present embodiment of FIG. 7, the possibility is illustrated to adjust, if desired, energy density depending on pressure and/or strain occurring in the actual building region during solidification of the material. A pressure/strain sensor 56 is brought into contact with the flexible film 75, optionally only during step of contacting part 9 with the flexible 75 carrying the material 7, during solidification by means of radiation exposure, and/or during the step of separating the part 9 now bearing the additionally solidified material from the flexible film 75.

Like in the embodiment of FIG. 6, it is a still further possible option that the energy density E delivered by the mask exposure system may be varied, if desired, in the exposed area of the building region, as basically explained in the previous embodiments (i.e. by delivering spatially distinct energy densities $E_0$, $E_1$, etc.).

As a further modification of the embodiment of FIG. 6 it is possible to replace projector unit 50 and reflector 45 by a mask exposure system for the selective delivery of electromagnetic radiation and/or synergistic stimulation.

Further modifications of the embodiments of FIGS. 6 and 7 are conceivable. For example it is possible to replace projector unit 50 and reflector 45 by a mask exposure system in FIG. 6, and vice versa to replace the mask exposure system 80 of FIG. 7 by another projection system, respectively for the selective delivery of electromagnetic radiation and/or synergistic stimulation.

The description of FIGS. 6 and 7 illustrate that when a freeform fabrication system based on a projection unit or a mask exposure unit is used, a fine tuning is reliably enabled depending on constitution and/or characteristics of a material to be solidified which contains a filler and a binder. The advantages according to the present invention are displayed independent whichever system used, e.g. a stereolithography system, a film transfer system or other freeform fabrication systems.

The embodiments described above can be combined, and they can be modified while still applying the principles of the present invention. It is further noted that the present embodiments have been described for illustrative purposes only, while various further modifications and variations are possible and can be applied by the person skilled in the art within the scope and gist of the present invention.

The invention claimed is:

1. A process for producing a three-dimensional object using an imaging unit comprising a predetermined number of discrete imaging elements or pixels, the process comprising:
    providing a material to be solidified, the material comprising a filler and a binder;
    delivering electromagnetic radiation or synergistic stimulation in a pattern or an image to a building region for solidifying said material;
    wherein said delivering of electromagnetic radiation and/or synergistic stimulation is performed selectively to a defined area or volume of said material to be solidified;
    wherein an energy density of electromagnetic radiation or synergistic stimulation is at least partially varied within said pattern or image by controlling a gray value or a color value of at least a part of the discrete imaging elements or pixels, and a variation of intensity of electromagnetic radiation or synergistic stimulation within said pattern or image is controlled by a control unit such that when the filler is a reflecting or scattering filler, an energy density of the electromagnetic radiation or synergistic stimulation delivered to a boundary region of said pattern or image is lower than an energy density of the electromagnetic radiation or synergistic stimulation delivered to an inner region of said pattern or image.

2. The process according to claim 1, wherein the material to be solidified is;
    a first material to be solidified for generating at least a part of a desired three-dimensional object structure, the first material comprising the filler and the binder, and
    the process further comprises providing a second material, different from said first material, to be solidified as another part of the desired three-dimensional object structure or as an auxiliary support structure;
    wherein delivering electromagnetic radiation or synergistic stimulation includes solidifying said first and second materials by means of the electromagnetic radiation or synergistic stimulation delivered selectively to respectively defined areas or volumes of said first and second materials; and
    wherein, energy densities of electromagnetic radiation or synergistic stimulation are at least partially varied between areas or volumes of said respectively defined first and second materials for solidification.

3. The process according to claim 1, wherein said selective delivery of electromagnetic radiation or synergistic stimulation comprises using a mask or a projection unit to deliver the electromagnetic radiation or synergistic stimulation selectively to the defined area or volume of material to be solidified.

4. The process according to claim 1, wherein said filler comprises ceramic particles.

5. The process according to claim 4, wherein said ceramic particles are selected from alumina particles or powders or zirconia particles or powders, or a mixture thereof.

6. The process according to claim 4, wherein said ceramic particles are powders of yttria stabilized tetragonal zirconia (YTZP), with or without a sintering additive or dispersion agent.

7. The process according to claim 1, wherein said filler is a powder or particles having a mean particle size in the range of about 0.1 nm to about 100 μm.

8. The process according to claim 1, wherein said binder is selected from the group consisting of photopolymers and adhesives.

9. The process according to claim 1, wherein said filler is contained in an amount of about 10% by weight to about 99% by weight of the total material to be solidified.

10. The process according to claim 1, wherein the binder of said material to be solidified comprises an adhesive which allows two or more layers, or other multiple structural parts of filler containing composite material to be successively attached together.

11. The process according to claim 1, wherein the three-dimensional object as produced is subjected to a post-treatment selected from post-hardening, de-binding, or sintering.

12. The process according to claim 1, wherein the three-dimensional object after solidifying the material has a first circumferential size in an untreated state and has a second circumferential size in a post-treated state, in particular in a sintered state, wherein said first circumferential size is larger than said second circumferential size.

13. The process according to claim 1, wherein the produced three-dimensional object is a dental product or a part of a dental product.

14. The process according to claim 1, wherein the three-dimensional object is built on an object carrier or support, wherein said object carrier or support is moved upward as the built three-dimensional object grows.

15. The process according to claim 1, wherein the material to be solidified is provided in the building region on a transparent film at the stage of delivering electromagnetic radiation or synergistic stimulation.

16. The process according to claim 1, wherein the material to be solidified comprises a photocurable resin as said binder.

17. The process according to claim 1, wherein the binder comprises a first binder substance and a second binder substance, and the first binder substance comprises a photocurable resin.

18. The process according to claim 1, wherein the material to be solidified is conveyed from a resin source to the building region on a movable film.

19. The process according to claim 18, wherein a mask projector is disposed below the film to project an image through the film.

20. The process according to claim 19, wherein the mask projector is a digital light projector.

21. The process according to claim 1, wherein the three-dimensional object is built on a object carrier or support placed above a device for delivering electromagnetic radiation or synergistic stimulation, and a transparent plate is disposed between said transparent object carrier or support and said radiation or synergistic stimulation delivery device.

22. A process for producing a three-dimensional object, comprising:

providing a material to be solidified, the material comprising a filler and a photocurable resin as a binder;

delivering electromagnetic radiation or synergistic stimulation in a pattern or an image to a building region for solidifying said material, the pattern or image having a first boundary region and a second inner region, and the electromagnetic radiation or synergistic stimulation delivered to the first boundary region corresponding to a gray value or a color value;

wherein said delivering of electromagnetic radiation or synergistic stimulation is performed selectively to a defined area or volume of said material to be solidified by using a mask projector;

wherein the three-dimensional object is built on an object carrier or support, and wherein said object carrier or support is moved upward as the built three-dimensional object grows; and wherein a variation of intensity of electromagnetic radiation or synergistic stimulation between said first boundary region and said section inner region is controlled by a control unit such that when the filler is a reflecting or scattering filler, the energy density of the electromagnetic radiation or synergistic stimulation delivered to the first boundary region of said pattern or image is lower than the energy density of the electromagnetic radiation or synergistic stimulation delivered to the second inner region of said pattern or image.

23. The process according to claim 22, wherein said mask projector is a digital light projector.

24. The process according to claim 22, wherein the material to be solidified is conveyed from a resin source to the building region on a transparent movable film.

25. A process for producing a three-dimensional object using an imaging unit comprising a predetermined number of discrete imaging elements or pixels, the process comprising:

providing a material to be solidified, the material comprising a filler and a binder;

delivering electromagnetic radiation or synergistic stimulation in a pattern or an image to a building region for solidifying said material, the pattern or image having a border region and an inner region, the border region having a first energy density of the delivered electromagnetic radiation or synergistic stimulation, and the inner region having a second energy density of the delivered electromagnetic radiation or synergistic stimulation; and adjusting the first energy density relative to the second energy density based on whether the filler is an absorbing filler or a reflecting or scattering filler.

26. The process according to claim 25, wherein the first energy density corresponds to a first energy intensity, the second energy density corresponds to a second energy intensity, and step of adjusting the first energy density relative to the second energy density comprises adjusting the first energy intensity relative to the second energy intensity.

27. The process according to claim 25, wherein the step of adjusting the first energy density relative to the second energy density based on the reflecting or scattering nature of the filler comprises adjusting a gray value or a color value of at least part of the pixels.

* * * * *

UNITED STATES PATENT AND TRADEMARK OFFICE
CERTIFICATE OF CORRECTION

| | |
|---|---|
| PATENT NO. | : 8,110,135 B2 |
| APPLICATION NO. | : 12/290003 |
| DATED | : February 7, 2012 |
| INVENTOR(S) | : Ali El-Siblani |

It is certified that error appears in the above-identified patent and that said Letters Patent is hereby corrected as shown below:

Column 22, Line 20, delete "section" and insert --second--.

Signed and Sealed this
Twentieth Day of March, 2012

David J. Kappos
*Director of the United States Patent and Trademark Office*